US011105785B2

(12) United States Patent
Artursson et al.

(10) Patent No.: US 11,105,785 B2
(45) Date of Patent: Aug. 31, 2021

(54) SYSTEM AND METHOD FOR ANALYZING DRILL CORE SAMPLES

(71) Applicant: MINALYZE AB, Sävedalen (SE)

(72) Inventors: Mikael Artursson, Jörlanda (SE); Axel Sjöqvist, Vårgårda (SE)

(73) Assignee: MINALYZE AB, Sävedalen (SE)

( * ) Notice: Subject to any disclaimer, the term of this patent is extended or adjusted under 35 U.S.C. 154(b) by 511 days.

(21) Appl. No.: 16/082,111

(22) PCT Filed: Jun. 3, 2017

(86) PCT No.: PCT/SE2017/050205
§ 371 (c)(1),
(2) Date: Sep. 4, 2018

(87) PCT Pub. No.: WO2017/155450
PCT Pub. Date: Sep. 14, 2017

(65) Prior Publication Data
US 2019/0107520 A1    Apr. 11, 2019

(30) Foreign Application Priority Data
Mar. 5, 2016    (SE) .................................... 1630051-9

(51) Int. Cl.
*G01N 33/24*    (2006.01)
*G01N 1/08*    (2006.01)
(Continued)

(52) U.S. Cl.
CPC ............. *G01N 33/24* (2013.01); *E21B 25/00* (2013.01); *E21B 25/005* (2013.01); *G01B 11/24* (2013.01);
(Continued)

(58) Field of Classification Search
CPC ........ G01N 33/24; G01N 1/08; E21B 25/005; G01B 11/24; G01B 11/30; G01V 11/00
See application file for complete search history.

(56) References Cited

U.S. PATENT DOCUMENTS 4,883,131 A † 11/1989 Foster
6,330,523 B1    12/2001 Kacyra et al.
(Continued)

FOREIGN PATENT DOCUMENTS

WO    1996/035941    † 11/1996
WO    2005/116392    † 12/2005
(Continued)

OTHER PUBLICATIONS

Extended European Search Report for European No. 17763656.0, dated Oct. 8, 2019 (9 pages).
(Continued)

*Primary Examiner* — Bryan Bui
(74) *Attorney, Agent, or Firm* — Kagan Binder, PLLC

(57) ABSTRACT

A System for collecting and processing data concerning physical features of drill core samples with three-dimensional shape and appearance. The system comprises a contact less analytical apparatus for measuring and collecting data of at least some part of the outer surface of the drill core samples, a first data-storing means for storing data collected by the analytical apparatus, a processing unit that applies one or more data evaluation algorithms on the data stored in the first data storage means in order to extract data regarding physical features of the drill cores (1) as an output, and a second data storage means for storage of the resulting output from the processing unit. The system is also related to a method for measuring and collecting data on the three-
(Continued)

dimensional shape and appearance of drill core samples, such as planar discontinuities including orientation marks on the drill core samples.

12 Claims, 4 Drawing Sheets

(51) Int. Cl.
*E21B 25/00* (2006.01)
*G01B 11/24* (2006.01)
*G01V 11/00* (2006.01)
*G01B 11/30* (2006.01)

(52) U.S. Cl.
CPC .............. *G01B 11/30* (2013.01); *G01N 1/08* (2013.01); *G01V 11/00* (2013.01)

(56) References Cited

U.S. PATENT DOCUMENTS

| | | | |
|---|---|---|---|
| 8,199,988 B2 † | 6/2012 | Marshall | |
| 8,385,604 B2 * | 2/2013 | Orpen | G01N 33/24 |
| | | | 382/109 |
| 9,741,106 B2 * | 8/2017 | Grader | G06T 7/0002 |
| 10,702,216 B2 * | 7/2020 | Sareen | H04N 5/232 |
| 2009/0080705 A1 | 3/2009 | Orpen | |
| 2014/0086381 A1 | 3/2014 | Grader et al. | |
| 2015/0146935 A1 | 5/2015 | Mezghani | |

FOREIGN PATENT DOCUMENTS

| | | |
|---|---|---|
| WO | 2005116392 A1 | 12/2005 |
| WO | 2010148435 A1 | 12/2010 |
| WO | 2011147017 A2 | 1/2011 |
| WO | 2011/146014 † | 11/2011 |
| WO | 2011146014 A1 | 11/2011 |
| WO | 2012069036 A1 | 5/2012 |
| WO | 2014142976 A1 | 9/2014 |

OTHER PUBLICATIONS

Tatone et al., "Quantitative Measurements of Fracture Aperture and Directional Roughness from Rock Cores", Rock Mechanics and Rock Engineering, vol. 45, No. 4, pp. 619-629, Jan. 24, 2012, (11 pages).

Paulsen et al., "A simple method for orienting drill core by correlating features in whole-core scans and oriented borehole-wall imagery" Journal of Structural Geology, vol. 24, No. 8, pp. 1233-1238, Aug. 1, 2002, (6 pages).

International Search Report for International Application No. PCT/SE2017/050205, dated May 5, 2018 (5 pages).

Swedish Search Report for Application No. 1630051-9, dated Mar. 5, 2016 (3 pages).

Olson, L., Samson, C., McKinnon, S.D., "3-D laser imaging of drill core for fracture detection and rock quality designation", International Journal of Rock Mechanics & Mining Sciences 73 (2015) 156-164, doi: 10.1016/j.ijrmms.2014.11.004.

* cited by examiner
† cited by third party

SYSTEM AND METHOD FOR ANALYZING DRILL CORE SAMPLES

CROSS-REFERENCE TO RELATED APPLICATIONS

This application claims priority to International Application No. PCT/SE2017/050205, filed Mar. 6, 2017 and titled "SYSTEM AND METHOD FOR ANALYZING DRILL CORE SAMPLES," which in turn claims priority from a Swedish Application having Ser. No. 1630051-9, filed Mar. 5, 2016 and titled "SYSTEM AND METHOD FOR ANALYZING DRILL CORE. SAMPLES," both of which are incorporated herein by reference in their entireties.

TECHNICAL AREA

The present invention relates to a system for collecting and processing data on the three-dimensional shape and appearance of drill core samples, e.g. drill core samples that are extracted during exploration for natural resources, including such data concerning characteristic physical features of those drill cores e.g. planar discontinuities, which system comprises a carrier for holding at least one drill core sample. The invention also relates to a method for measuring, collecting and processing data on the three-dimensional shape and appearance of drill core samples, e.g. such drill core samples that are extracted during exploration for natural resources, including the characteristic physical features of those drill cores such as planar discontinuities and also including orientation marks on the drill core samples' surfaces, the method including spatial analysis of the data, e.g. to calculate the orientation of discontinuities relative to the drill core sample axis and orientation line.

BACKGROUND

Exploration of the above-mentioned type has long been performed in such a way that, after having found a location with an indicated deposit through well-known methods, an exploration drilling is performed in order to obtain a better basis for a subsequent decision on a full investment in further mining operations. During exploration drilling, cores are extracted and then later analyzed in detail.

When having extracted drill cores in the field from boreholes, the cores are usually divided into samples of typical lengths around 1 meter and then stored a few cores together in purpose-made trays. The number of samples in each tray is usually 4-6, and they are usually separated in separate compartments and marked regarding original orientation in the bore hole and order of extraction.

Among the drill cores there are a number of cores that contain discontinuities and other physical features of those drill cores e.g. mineral fabric, and it is of great value to obtain data on the location and angles of these discontinuities relative to the core axis and the original position in the bore hole of the cores, since the discontinuities in the drill core are a representation of discontinuities in the bedrock being drilled.

When looking for discontinuities, the samples are characterized by ocular inspection. Natural planar discontinuities can be measured be their Alpha and Beta angles, the angles being relative to an orientation line on the core sample, applied when extracting the cores from the drill hole in e.g. bedrock, and a longitudinal axis of the core sample. It is also obviously important that the discontinuities are always documented with respect to borehole and core sample depth.

One means for measuring the discontinuities is by using a goniometer that is essentially a short tube of see-through material, which tube comprises marked angle lines and degrees scales around its outer surface area. The tube is positioned with the drill core to be analyzed inside, and by moving it along the core, discontinuities can be measured and documented by comparing the angles of the discontinuity in question with the marking on the tube. One such tube is marketed under the Trade Mark EZY LOGGER. Due to that the measurement, using the EZY LOGGER, is made by ocular inspection and manual recording, it is almost impossible to quality control and reproduce the measurement.

Another way of analyzing is to use the equipment and method that is described in the patent application US2009/0080705, where a 2D photo is used in cooperation with a core holding box that has calibrated walls for calibrating the 2D photo. This method uses simplifications and assumptions that affects the evaluation.

The common problem with the above approaches is that it is a manual process which can produce a lot of false data.

SUMMARY OF THE INVENTION AND ITS ADVANTAGES

An embodiment of the presently presented system for improving the above related process of analyzing drill core structures comprises the following:

a. a contactless analytical apparatus (5) for measuring and collecting data on the three-dimensional shape and appearance of at least some part of the outer surface of drill core samples (1), where the cores have a reference line (15), which is indicating the "rotational" position the core had in its original place in the bore hole, b. a first data-storing means (21) for storing data collected by the analytical apparatus as a 3D representation, c. a processing unit that applies one or more data evaluation algorithms on the data stored in the first data storage means (21) in order to extract data regarding physical features, including the reference line, of the drill cores (1) as an output, referring to the reference line (15) and a longitudinal axis (16) of the core, and d. a second data-storing means for storage of the resulting output from the processing unit.

With the presented system, structure data can automatically or semi-automatically be derived from the individual drill cores while also the accuracy of the derived data is improved compared to state of the art technique.

In an embodiment of the system the contactless analytical apparatus comprises a light-based 3D sensor or a laser 3D sensor. This type of sensors are easily adapted to generate 3D representations, e.g. point clouds that can be the basis for the analysis wanted and thus the collected data can be stored as a point cloud for each drill core in the first data storage means. An option is to also generate and store three dimensional polygon meshes based on the point clouds in order to be able to generate a visual representation which is more picture-like. The laser system can be of a linear system type.

An embodiment of the invention the system includes a means for creating an image of the core and means for overlaying the image on the 3D point clouds. This would be a combined representation which is very informative to a viewer of a visual representation. The image, or graphic representation, can be a photographic or digital picture.

One further embodiment the system comprises a visualization means for presenting data generated by the system. With this as an information source an operator can operate the system and e.g. choose and feed parameters for entering into the system and its processor.

In another embodiment of the system, wherein the system comprises a component analyzing unit for analyzing elements like minerals etcetera in the core samples and wherein the component analyzing unit is movably arranged and dependent on a distance controlling means for control of the distance between the component analyzing unit and the cores being analyzed, information from the processing unit is used to calculate the distance input to the distance controlling means. The component analyzing means can then suitably be of an X-ray type. This is component saving as the distance controlling means in this case does not need a distance sensor of its own. The component analyzer unit can suitably be of an X-ray type.

A method according to the invention comprises the steps of
a. using a contactless analytical apparatus for measuring and collecting data on the three-dimensional shape and appearance of at least some part of the outer surface of drill core samples, where the cores have a reference line (15), which is indicating the "rotational" position the core had in its original place in the bore hole
b. storing of the collected data in a first data-storing means as a 3D representation,
c. selecting input parameters to mathematical algorithms that are able to create a calculation of a given physical feature in the drill core sample from the collected and stored data combined with the input parameters,
d. performing a three-dimensional analysis of physical features of the drill core samples by processing the collected data stored in the first data storing means and selected parameters in a data processing unit, while relating the analysis to a spatial position of the feature in the drill core samples, referring to the reference line (15) and a longitudinal axis (16) of the core, and storing the results of the three-dimensional analysis.

The Method advantageously uses a contactless analytical apparatus like a light-based 3D sensor, the output of which is used to generate point clouds as the basis for the analysis. The collected data is stored as point clouds, representing individual drill cores, in the first data-storing means.

Further, the point clouds are advantageously used as the basis for creating 3D polygon meshes, comprised in the 3D representation. An option is to create an image of each core and to overlay the image on the respective drill core 3D point cloud to a combined visualization representation.

The system can be both manually and automatically operated, the later under complete control of a processing unit, implemented by appropriate software.

SUMMARY OF THE DRAWINGS

The invention will hereinafter be further described and explained in connection with embodiments shown in the attached drawings, wherein.

The drawings are identical to those of the priority application, SE1630051-9.

DESCRIPTION OF EMBODIMENTS

Figure 1:
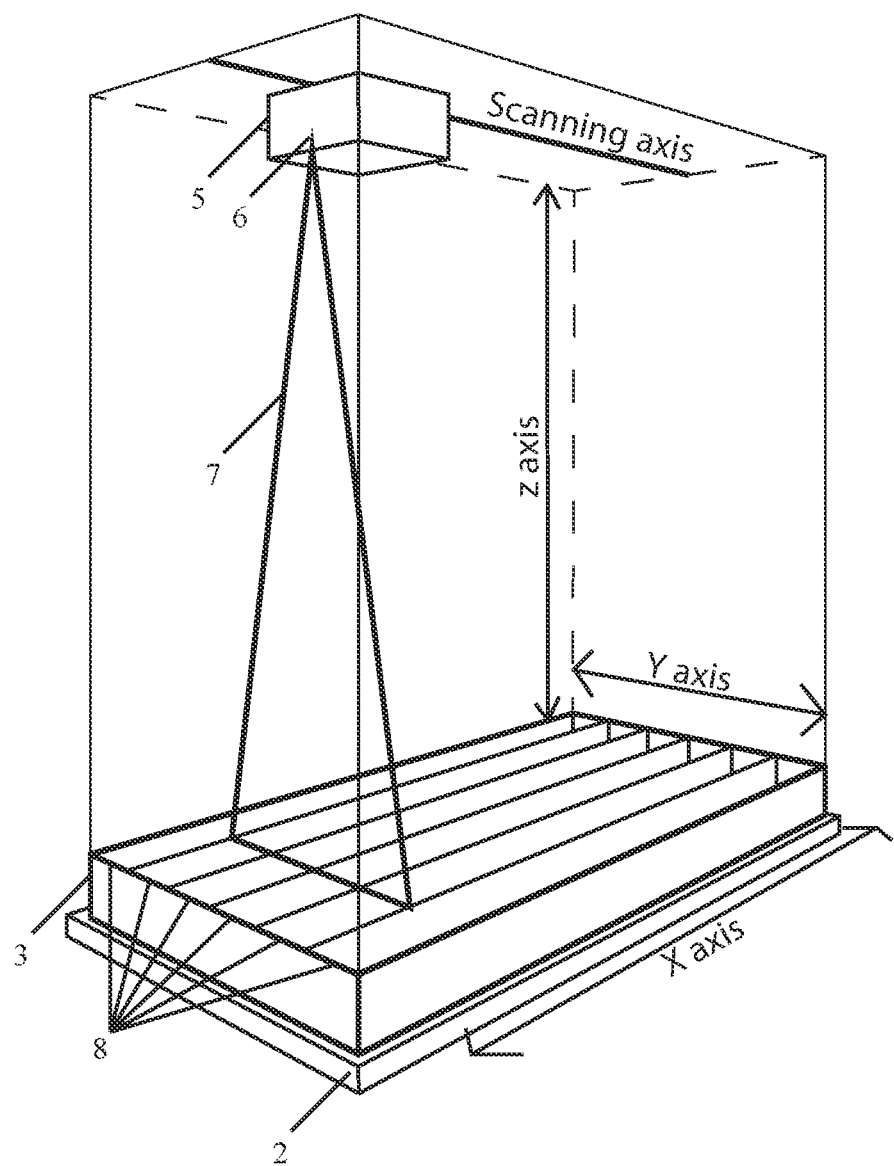
FIG. 1 shows schematically a system set-up with a carrier for drill cores in scanning position with a 3D scanner.

FIG. 1 shows schematically a set up for a three-dimensional scanning of drill cores, taken from bedrocks etcetera. The different components shown in the set up are arranged in a supporting lattice or framework (not shown).

The disclosed embodiment is designed to comprise a laser distancing and ranging arrangement. Thus a scanning unit 5 is arranged above (as seen in the figure but not shown in detail.) a tray 3, which tray in turn is placed on a carrier 2. The tray 3 is designed to be able to house up to 6 drill cores (not shown) in compartments 8. The scanning unit 5 comprises a digital laser/detector unit which comprises a laser, generating a laser beam, and a distance measuring detector means, optically following the laser spot as it is hitting a target, the spot being arranged to sweep linearly transversely over the core to be measured at the moment, one core after the other. The scanning unit thus measures along the laser curve, at a large number of points, with a high resolution, the full distance of points on the particular curve following the object to be scanned. This generates digitally a curve point cloud, representing a distance curve following the laser line, as the laser beam hits the object to be measured. In the figure the linear laser beam path 7 is shown covering several compartments 8, but generally only one drill core in a single compartment is scanned at a time.

As can be seen in the FIG. 1, the scanning unit 5 is movably arranged along an axis and thus can move back and forward in directions marked by X-axis, equally to Scanning axis. So, while scanning from one end of a drill core (not shown) to the other, the scanning unit 5 is arranged, with equidistant small steps in the X directions, to generate a series of digital curve point clouds, with a given resolution, parallel to the Y axis. Added together, those curve point clouds form a 3D representation of the core surface. A scanning unit like the scanning unit 5 is marketed by the company Sitek AB as a "Non-contact distance measurement system". There is also a unit called "Optocator" marketed by LMI3D. With reference to FIG. 1, the scanning unit 5 is movably arranged with known technology in Z-directions and the carrier 2 is in similar way movable in Y-directions, in order to bring selected cores in scanning position, into the laser field of view, for the scanning unit. Since the cores are mainly cylindrical, the field of view covers nearly 180 degree around the circumference of the core.

Figure 2:
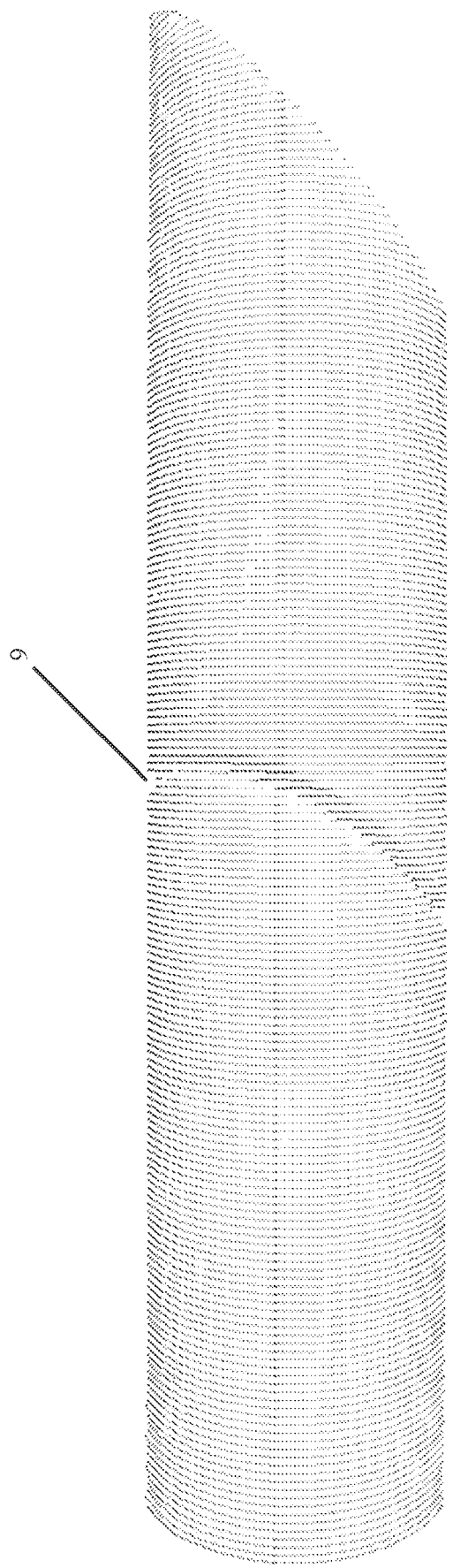
FIG. 2 shows 3D point cloud containing a projection of a discontinuity in a core sample.

A 3D representation, as mentioned above, can be shown as in FIG. 2 as a point cloud, in which each individual point also contains data about RGB or greyscale colour, which, if presented on a display, can be interpreted as a "picture". The resolution of the point cloud in FIG. 2 is changed in order to be clearer to the viewers. In FIG. 2 can be seen a discontinuity 9. The discontinuity and its position and Alpha and Beta angles can be analyzed as shall be explained below. Also, in FIG. 2, a reference line, shown along the drill core is present in the middle of the FIG. 2. The reference line is made of paint or of a similar material, of a type clearly visible to the scanning unit.

Figure 3:
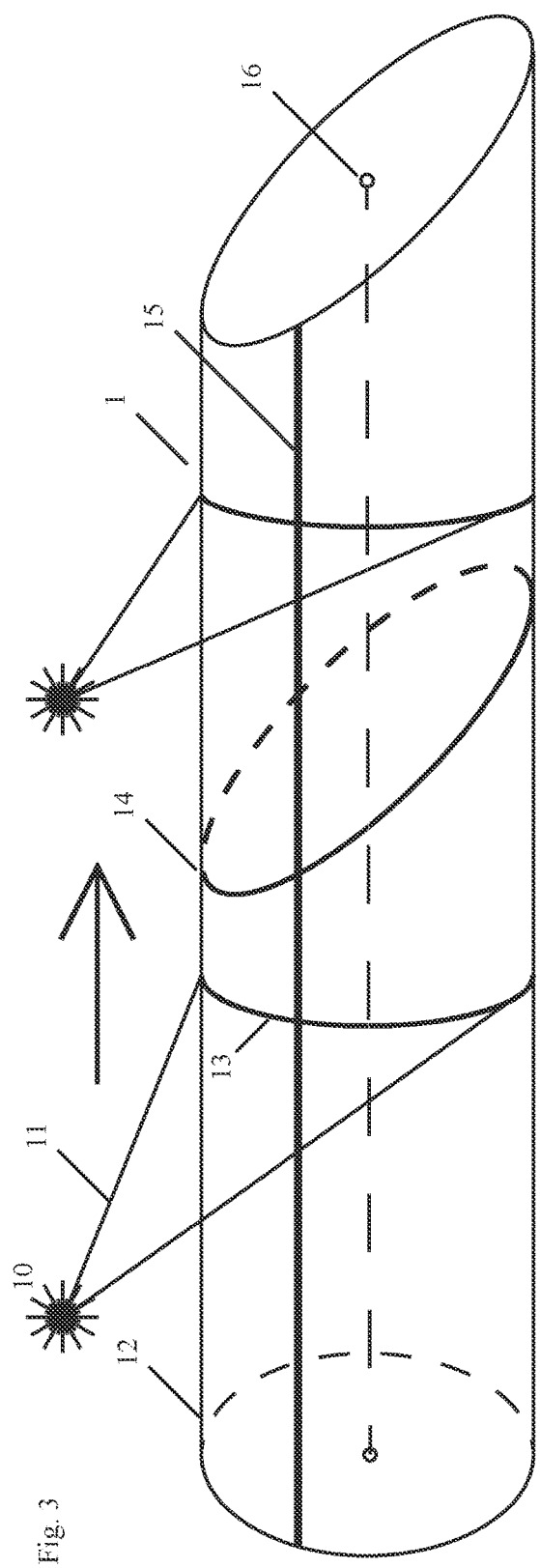
FIG. 3 shows schematically a core sample being scanned by a 3D line scanning laser equipment.

In FIG. 3, which shows schematic representation of a drill core (here with lines and curves instead of a point cloud like the representation in FIG. 2), a laser/detector unit with its radiation shown as a laser output 10 and a sweeping laser beam 11. As the laser beam sweeps, following a sweeping line transverse to the longitudinal axis of the core 1, it hits a part of the curved surface 12 of a mainly cylindrical drill core, positioned beneath the laser in a tray as described above, and a laser spot curve 13 is generated. The laser field of view, as is shown, covers almost half the circumference of the core. On the part of the half of the core that can be seen, the core has a reference line 15, which is indicating the "rotational" position the core had in its original place in the bore hole, similar to as shown in FIG. 2. The core is of course placed in the tray in such a way that the reference line is "visible", within the field of view, for the scanning unit. The core is also shown with its longitudinal axis 16 marked. During the sweeping action over the core, the detector means measures the distance of a large number of points along the curved surface, generating a curve point cloud. After that one curve point cloud is completed, the scanning unit generates, with very small incremental steps, repeatedly, curve point clouds along the core. As can be seen in FIG. 3, a discontinuity 14 is present in the drill core.

Figure 4:
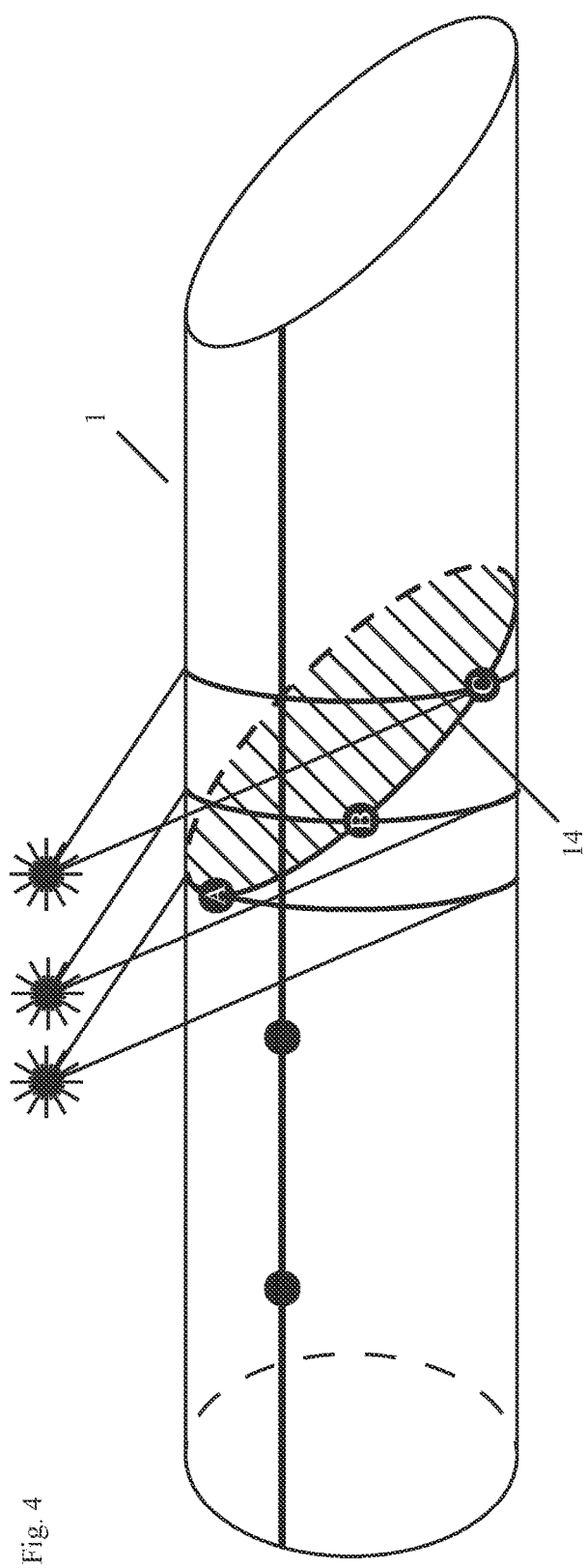
FIG. 4 shows schematically a part of a 3D representation of a drill core where a discontinuity is identified and FIG. 5 shows a block diagram illustrating a method according to the present disclosure.

In FIG. 4 is shown a drill core as in FIG. 3. The discontinuity 14 is marked with three dots, A, B and C. The points A, B and C are marked on three different, separately localized data points from the point cloud corresponding to the drill core seen in FIG. 2, which points are generated as the scanning unit has scanned the core 1. The points A, B and C are here chosen manually by a system operator, but with a computer data analyzing software they can be chosen automatically. Since the "picture" is a digital, three-dimensional point cloud, the three points together define a plane in a three-dimensional space, which intersects the core, and this plane is a good representation of a specific crack in the bedrock, surrounding the bore hole the core is lifted from. Referring now to the reference line 15 and the longitudinal axis 16 of the core, the angles Alpha and Beta of the discontinuity and thereby the crack plane can be calculated by proper software in a computer or a similar processing unit.

Figure 5:
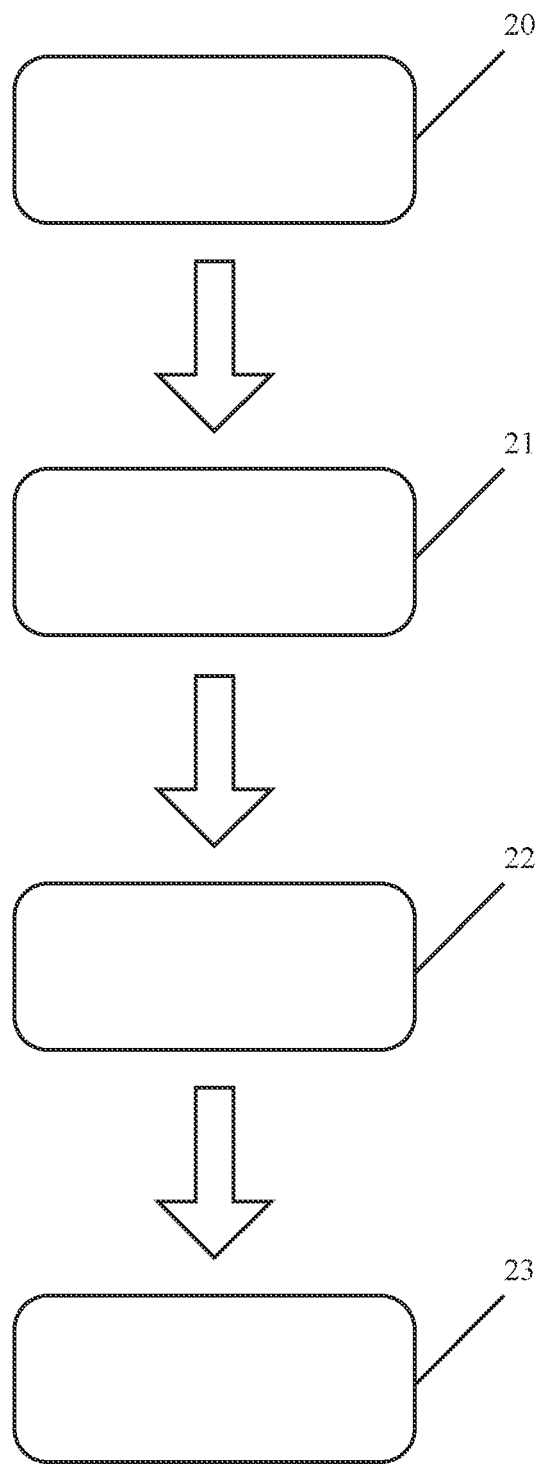

FIG. 5 shows a block diagram explaining a method for extracting information of a three-dimensional point cloud representing the appearance of a three-dimensional object, in this case especially a drill core.

According to this disclosure, an analytical apparatus for contactless measuring and collecting data on the three-dimensional shape and appearance of at least some part of the outer surface of a drill core sample is used, generating data in a step 20.

The data collected in block 20 is used as an input for a second block step, comprising storing of the collected data in a first data-storing means 21 as 3D representation of the respective drill core.

For processing of data collected and stored in the first data-storing means 21, input parameters are selected from the stored data and used as selected input in step 22 to mathematical algorithms that are able to create a calculation of a given physical feature in the drill core sample from the stored data combined with the input parameters, e.g physical properties of the drill core.

In the last block 23, finally, comprising a second data storage means, the three-dimensional data stored in the first data storage means 21 is processed in a processing unit with the selected parameters, performing a three-dimensional analysis of physical features of the drill core samples, while relating the analysis to the spatial position of the feature in the drill core samples, i.e. referring to the reference line 15 and the longitudinal axis 16. The results of the three-dimensional analyses are stored in the second data storage means. The first data storing means and the second data storage means can be combined.

The 3-D representation generated by the system and method are advantageously presented for e.g. an operator on a visualization means like a data screen. As seen in FIG. 2, the point clouds can be shown and understood as a 3D representation. For some purposes, another type of presentation can be achieved if the point cloud is processed to generate polygon meshes. And, if wanted, an image, like a digital picture can be taken by an image means of a known type comprised in the system, like a digital camera, (not shown) of the individual drill cores and overlaid the respective polygon meshes representation to a combined visual representation.

The invention is not limited to the example disclosed and explained above.

The processing unit can be an ordinary computer or a customized data processor, designed for the task. The data evaluation algorithms and other software can be designed in different ways, known and available for a software specialist.

It is not necessary to use a multi drill core tray, but single drill cores can be analyzed as well, with a system designed for that but still using the invention.

The 3D scanner can be of other type as present on the market as long as it generates a digital three-dimensional data of the scanning object. The laser beam can be arranged in a direction along the longitudinal axis of the core sample to be scanned. The calculation of the plane of a discontinuity can be maid manually, by choosing points in the point cloud representing the surface of the core sample, but can also be made by a computer data analyzing system. The first and second data-storing means can physically be the same.

The invention can be used in a system described in WO2011/146014, the content of which is hereby incorporated in this application. This system can be used in combination with a component analyzing unit, using the same scanning unit output for evaluating and holding the wanted distance between the component analyzing unit and the core sample to be analyzed.

The system and method is also well suited for exploration and analyzing the ground, bedrocks and the like when planning for construction work like tunnels and buildings of different kinds, where information on ground stability is very important. It not limited to ground rocks only but can be used for analyzing other types of drill cores, e.g. concrete drill cores.

It is especially adapted to generate data of Alpha and Beta angles of discontinuities and other planar structures in the core samples, the angles being measured relative to an orientation line on the core sample and a longitudinal axis of the core sample. The system comprises a carrier for holding at least one core sample and an analyzing unit. The invention also relates to a method for analyzing the structure of drill core samples, e.g. drill core samples that are extracted during the exploration of natural resources such as ore, oil and gas. It is especially adapted to generate information of Alpha and Beta angles of discontinuities in the core samples, the angles being measured relative to an orientation line on the core sample and a longitudinal axis of the core sample.

The physical features sought can be planar discontinuities, geological fabric, ore veins, drill core radius or core volume. Different algorithms apply for different features.

The analysis can include calculation of the acute angle between the drill core axis and the semi-major axis of the elliptical intersection of a plane and the drill core sample (alpha angle) or the rotational angle around the drill core axis between the drill core orientation line and the semi-major axis of the elliptical intersection of a plane and the drill core sample (beta angle) The drill core samples can be such that are extracted during exploration for natural resources, such as mineral resources, oil, and gas, and/or for inspection of bedrock or concrete structures of buildings or construction creations like walls e.g of dams.

The invention claimed is:

1. A system for analyzing a drill core samples, said drill core sample including a planar discontinuity and being provided with a reference line indicating an original rotational position of the drill core in a bore hole, which system comprises
   a contactless analytical apparatus,
   a carrier for holding the drill core sample such that the reference line is visible to the contactless analytical apparatus,
   wherein the contactless analytical apparatus is configured to generate a plurality of curve point clouds, each curve point cloud including distances to a number of points located along a line on an outer surface of the drill core transverse to a longitudinal axis of the drill core, and data about at least one color and greyscale of each point,
   a data-storing means for storing a 3D representation based on the plurality of curve point clouds, said 3D representation corresponding to a field of view covering nearly 180 degrees of the circumference of the drill core,
   a processing unit configured to analyze the drill core sample by:
      presenting the 3D representation as a picture on a display, said planar discontinuity being visible in the picture,
      allowing a user to indicate three points (A, B, C) located along said planar discontinuity,
      calculating at least one of
   a) an acute angle (alpha) between 1) the longitudinal axis and 2) a major axis of an elliptical intersection of the drill core and the planar discontinuity, and
   b) a rotational angle (beta) between the reference line and said major axis.

2. The system according to claim 1, wherein the contactless analytical apparatus comprises a light-based 3D sensor.

3. The system according to claim 1, wherein the 3D representation is stored as a point cloud in the data-storing means.

4. The system according to claim 3, wherein the 3D representation is stored as a polygon mesh generated from the curve point clouds.

5. The system according to claim 4, wherein the system comprises means for creating an image of the core and means for overlaying the image on the polygon mesh.

6. The system according to claim 1, wherein the system comprises a component analyzing unit for analyzing elements like minerals etcetera in the core samples, the component analyzing unit being movably arranged and dependent on a distance controlling means for control of the distance between the component analyzing unit and the cores being analyzed, wherein information from the processing unit is used to calculate the distance input to the distance controlling means.

7. The system according to claim 6, wherein the component analyzing unit is of an X-ray type.

8. A method for analyzing a drill core sample, said drill core including a planar discontinuity and being provided with a reference line indicating an original rotational position of the drill core in a bore hole, the method comprising the steps of:
   holding the drill core sample such that the reference line is visible to the contactless analytical apparatus,
   using the analytical apparatus to generate a plurality of curve point clouds, each curve point cloud including distances to a number of points located along a line on an outer surface of the drill core transverse to a longitudinal axis of the drill core, and data about at least one of color and greyscale of each point,
   storing a 3D representation based on the plurality of curve point clouds in a data-storing means, said 3D representation corresponding to a field of view covering almost half of the circumference of the drill core,
   localizing said planar discontinuity by:
      presenting the 3D representation as a picture on a display, said planar discontinuity being visible in the picture,
      allowing a user to indicate three points (A, B, C) located along said planar discontinuity,
      calculating, in a processing unit, at least one of
   a) an acute angle (alpha) between 1) the longitudinal axis and 2) a major axis of an elliptical intersection of the drill core and the planar discontinuity, and
   b) a rotational angle (beta) between the reference line and said major axis.

9. The method according to claim 8, where the contactless analytical apparatus comprises a light-based 3D sensor.

10. The method according to claim 8, wherein the 3D representation is stored as a polygon mesh generated from the curve point clouds.

11. The method according to claim 10, comprising creating an image of the core and overlaying the image on the polygon mesh to a combined visualization representation.

12. The method according to claim 8, wherein the 3D representation is stored as a point cloud in the data-storing means.

* * * * *

UNITED STATES PATENT AND TRADEMARK OFFICE
CERTIFICATE OF CORRECTION

| | | |
|---|---|---|
| PATENT NO. | : 11,105,785 B2 | Page 1 of 1 |
| APPLICATION NO. | : 16/082111 | |
| DATED | : August 31, 2021 | |
| INVENTOR(S) | : Mikael Artursson and Axel Sjöqvist | |

It is certified that error appears in the above-identified patent and that said Letters Patent is hereby corrected as shown below:

On the Title Page

(22) PCT Filed: please delete "Jun. 3, 2017" and insert in place thereof --Mar. 6, 2017--.

Signed and Sealed this
Tenth Day of May, 2022

*Katherine Kelly Vidal*

Katherine Kelly Vidal
*Director of the United States Patent and Trademark Office*